United States Patent
Grubel et al.

(10) Patent No.: US 10,152,609 B2
(45) Date of Patent: Dec. 11, 2018

(54) PERSONALLY IDENTIFIABLE INFORMATION (PII) DISCLOSURE DETECTION

(71) Applicant: THE BOEING COMPANY, Chicago, IL (US)

(72) Inventors: Brian C. Grubel, Chicago, IL (US); Brian P. Treich, Chicago, IL (US)

(73) Assignee: THE BOEING COMPANY, Chicago, IL (US)

( * ) Notice: Subject to any disclaimer, the term of this patent is extended or adjusted under 35 U.S.C. 154(b) by 255 days.

(21) Appl. No.: 14/807,765

(22) Filed: Jul. 23, 2015

(65) Prior Publication Data

US 2017/0024581 A1 Jan. 26, 2017

(51) Int. Cl.
| | |
|---|---|
| *G06F 21/62* | (2013.01) |
| *G06F 19/00* | (2018.01) |
| *G06F 17/30* | (2006.01) |
| *H04L 29/06* | (2006.01) |
| *G16H 10/60* | (2018.01) |

(52) U.S. Cl.
CPC ...... *G06F 21/6245* (2013.01); *G06F 17/3053* (2013.01); *G16H 10/60* (2018.01); *H04L 63/0407* (2013.01); *H04L 63/1408* (2013.01)

(58) Field of Classification Search
CPC ............. G06F 21/6245; G06F 17/3053; G06F 19/322; H04L 63/0407; H04L 63/1408
See application file for complete search history.

(56) References Cited

U.S. PATENT DOCUMENTS 8,887,273 B1 * 11/2014 Satish .................... G06Q 20/02
726/22
2007/0266079 A1 11/2007 Criddle et al.
2012/0291087 A1 * 11/2012 Agrawal .................. G06F 21/55
726/1
2013/0318199 A1 * 11/2013 Le Jouan ................ H04L 67/02
709/217
2015/0088777 A1 3/2015 Chauhan et al.

FOREIGN PATENT DOCUMENTS

WO WO-2010011182 A2 * 1/2010 ............. G06F 21/16
WO 2011/150261 A1 12/2011

OTHER PUBLICATIONS

Combined Search and Examination Report under Sections 17 and 18(3) issued in UK Application No. GB1608631.6 dated Oct. 21, 2016, Applicant: The Boeing Company (7pages).

* cited by examiner

*Primary Examiner* — Noura Zoubair
(74) *Attorney, Agent, or Firm* — Haynes and Boone, LLP

(57) ABSTRACT

Systems, methods, and apparatus of tracking user information dissemination are disclosed herein. In one or more embodiments, the disclosed method involves matching, by a processor(s), a first service provider(s) to an address(es) (e.g., an email address and/or a postal address) related to a user(s) and/or personal identifiable information (PII) related to the user(s). The method further involves aggregating, by a processor(s), the number of times a second service provider(s) utilizes the address(es) to mail the user(s) and/or sends at least a portion of the PII to the user(s) and/or to another user(s). Further, the method involves generating, by the processor(s), a ranking of trustworthiness for the first service provider(s) based on the number of times all of the second service provider(s) utilizes the address(es) to mail the user(s) and/or sends at least a portion of the PII to the user(s) and/or to another user(s).

21 Claims, 13 Drawing Sheets

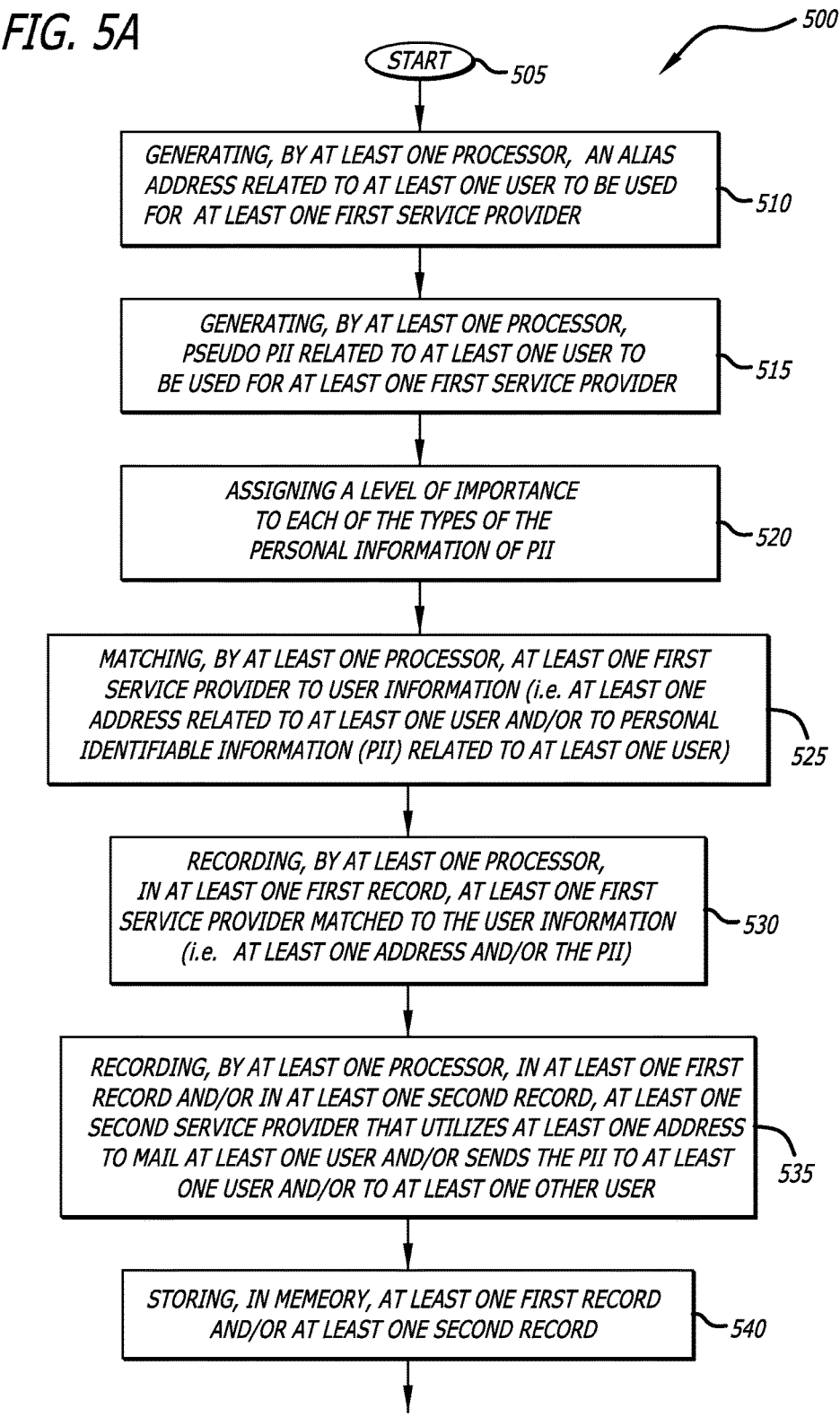

Record 1

| real user name | real email address | service provider | user name for service provider | email for service provider | birthday for service provider | cell phone for service provider |
|---|---|---|---|---|---|---|
| John Doe | john.doe@gmail.com | Store A | John Smith | john.doeaudDieoj@gmail.com | January 1, 1970 | 555-867-5309 |
| John Doe | john.doe@gmail.com | Store B | John Jones | johndoeoxzHwsu@gmail.com | January 1, 1972 | 571-541-2746 |
| David Johnson | david@cox.net | Store C | Dave Jameson | davidjwoxUxkdo@cox.net | December 2, 1980 | 310-346-2212 |
| David Johnson | david@cox.net | Store D | John Davidson | davidiqtkGvisc@cox.net | December 2, 1980 | 333-245-1880 |
| David Johnson | david@cox.net | Store E | David Johnson | davidjiskRtvbg@cox.net | December 2, 1980 | 212-545-6783 |
| ... | ... | ... | ... | ... | ... | ... |
| ... | ... | ... | ... | ... | ... | ... |
| ... | ... | ... | ... | ... | ... | ... |
| ... | ... | ... | ... | ... | ... | ... |
| ... | ... | ... | ... | ... | ... | ... |

| | | Record 2 | | | | | |
|---|---|---|---|---|---|---|---|
| real user name | real email address | service provider | third party service provider | user name for service provider Received | email for service provider received | birthday for service provider received | cell phone for service provider received | Information not received by service provider |
| John Doe | john.doe@gmail.com | Store A | Store F | x | x | x | x | N/A |
| John Doe | john.doe@gmail.com | Store B | N/A | N/A | N/A | N/A | N/A | N/A |
| David Johnson | david@cox.net | Store C | N/A | N/A | N/A | N/A | N/A | N/A |
| David Johnson | david@cox.net | Store D | N/A | N/A | N/A | N/A | N/A | N/A |
| David Johnson | david@cox.net | Store E | Store G | x | x | N/A | x | home address:34 Gingerwood Avenue, Irvine, CA 92603 |
| ... | ... | ... | ... | ... | ... | ... | ... | |
| ... | ... | ... | ... | ... | ... | ... | ... | |
| ... | ... | ... | ... | ... | ... | ... | ... | |
| ... | ... | ... | ... | ... | ... | ... | ... | |
| ... | ... | ... | ... | ... | ... | ... | ... | |
| ... | ... | ... | ... | ... | ... | ... | ... | |

1010

FIG. 10B

PERSONALLY IDENTIFIABLE INFORMATION (PII) DISCLOSURE DETECTION

FIELD

The present disclosure relates to personally identifiable information (PII). In particular, it relates to PII disclosure detection.

BACKGROUND

Currently, personal information and/or mailing contact information (e.g., an email address or a postal address) related to users is often sold or distributed to third parties after a user signs up for a web service with an internet service provider. Because a user does not know where a third party received the user's information, the user cannot make an informed decision regarding whether to share their information when signing up for a web service. As such, there is a need for an improved technique for tracking the dissemination of user personal information to third parties, and for providing users with information regarding which internet service providers are disseminating user personal information.

SUMMARY

The present disclosure relates to a method, system, and apparatus for personally identifiable information (PII) disclosure detection. In one or more embodiments, a method of tracking user information dissemination involves matching, by at least one processor, at least one first service provider to at least one address related to at least one user and/or personal identifiable information (PII) related to at least one user. The method further involves aggregating, by at least one processor, a number of times at least one second service provider utilizes at least one address to mail at least one user and/or sends at least a portion of the PII to at least one user and/or to at least one other user. Further, the method involves generating, by at least one processor, a ranking of trustworthiness for at least one first service provider based on the number of times all of at least one second service provider utilizes at least one address to mail at least one user and/or sends at least a portion of the PII to at least one user and/or to at least one other user.

In one or more embodiments, the method further involves recording, by at least one processor, at least one first service provider matched to at least one address and/or the PII.

In at least one embodiment, the method further involves recording, by at least one processor, at least one second service provider that utilizes at least one address to mail at least one user and/or sends the PII to at least one user.

In one or more embodiments, at least one processor records, in at least one first record, at least one first service provider matched to at least one address and/or the PII. In some embodiments, at least one processor records, in at least one second record, at least one second service provider that utilizes at least one address to mail at least one user and/or sends at least a portion of the PII to at least one user.

In at least one embodiment, at least one processor records, in at least one first record, at least one first service provider matched to at least one address and/or the PII. In some embodiments, at least one processor records, in at least one first record, at least one second service provider that utilizes at least one address to mail at least one user and/or sends at least a portion of the PII to at least one user.

In one or more embodiments, at least one address is an email address and/or a postal address. In at least one embodiment, at least one address is a usable address and/or an alias address. In some embodiments, the method further involves generating, by at least one processor, the alias address related to at least one user to be used for at least one first service provider.

In at least one embodiment, the PII is real PII and/or pseudo PII. In some embodiments, the method further involves generating, by at least one processor, the pseudo PII related to at least one user to be used for at least one first service provider.

In one or more embodiments, the PII comprises different types of personal information. In some embodiments, the types of personal information comprise a name, billing address, shipping address, home phone number, work phone number, mobile phone number, birth date, occupation, employer, employer address, income, credit card information, and/or user identification (ID). In at least one embodiment, the method further involves assigning, by at least one processor and/or user, a level of importance to each of the types of the personal information of the PII. In some embodiments, the ranking of trustworthiness for at least one first service provider is further based on the level of importance of the types of personal information of the PII that at least one second service provider sends to at least one user.

In at least one embodiment, the method further involves displaying, on a display screen, the ranking of trustworthiness for at least one first service provider.

In one or more embodiments, the method further involves displaying, on a display screen, a map showing the relationship for sharing the user information between at least one first service provider and at least one second service provider.

In at least one embodiment, a system of tracking user information dissemination involves at least one processor to match at least one first service provider to at least one address related to at least one user and/or personal identifiable information (PII) related to at least one user; to aggregate the number of times at least one second service provider utilizes at least one address to mail at least one user and/or sends at least a portion of the PII to at least one user and/or to at least one other user; and to generate a ranking of trustworthiness for at least one first service provider based on the number of times all of at least one second service provider utilizes at least one address to mail at least one user and/or sends at least a portion of the PII to at least one user and/or to at least one other user.

In one or more embodiments, at least one processor is further to record at least one first service provider matched to at least one address and/or the PII.

In at least one embodiment, at least one processor is further to record at least one second service provider that utilizes at least one address to mail at least one user and/or sends the PII to at least one user.

In one or more embodiments, the system further involves a display screen to display the ranking of trustworthiness for at least one first service provider.

In at least one embodiment, the system further involves a display screen to display a map showing a relationship for sharing the user information between at least one first service provider and at least one second service provider.

The features, functions, and advantages can be achieved independently in various embodiments of the present disclosure or may be combined in yet other embodiments.

DRAWINGS

These and other features, aspects, and advantages of the present disclosure will become better understood with regard to the following description, appended claims, and accompanying drawings where:

FIGS. 5A and 5B are flow charts depicting the disclosed detailed method for PII disclosure detection, in accordance with at least one embodiment of the present disclosure.

FIG. 6 is a flow chart depicting the disclosed method for PII disclosure detection, where a unique alias email address is matched to a service provider, in accordance with at least one embodiment of the present disclosure.

FIG. 7 is a flow chart depicting the disclosed method for PII disclosure detection, where a unique alias email address and real PII is matched to a service provider, in accordance with at least one embodiment of the present disclosure.

FIG. 8 is a flow chart depicting the disclosed method for PII disclosure detection, where a usable email address and real PII is matched to a service provider, in accordance with at least one embodiment of the present disclosure.

FIG. 9 is a flow chart depicting the disclosed method for PII disclosure detection, where a usable email address (or alias email address) and pseudo PII is matched to a service provider, in accordance with at least one embodiment of the present disclosure.

FIG. 10A is a diagram showing an exemplary first record, which shows the email addresses and PII matched to service providers, that may be employed by the disclosed system for PII disclosure detection, in accordance with at least one embodiment of the present disclosure.

FIG. 10B is a diagram showing an exemplary second record, which shows the email addresses and/or PII received by third party service providers, that may be employed by the disclosed system for PII disclosure detection, in accordance with at least one embodiment of the present disclosure.

DESCRIPTION

Figure 1:
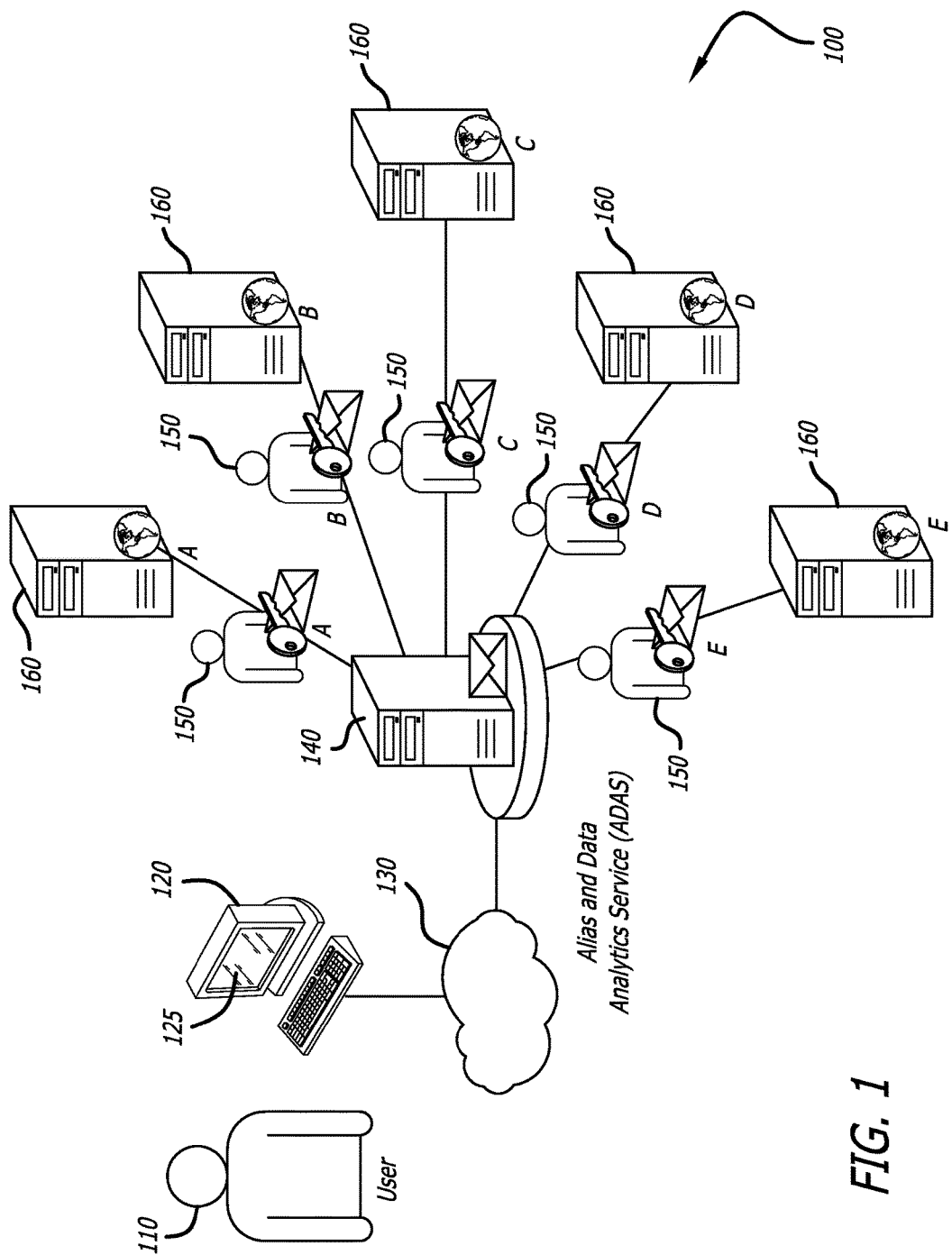
FIG. 1 is a diagram showing the disclosed system for personally identifiable information (PII) disclosure detection, where an email address and/or PII is matched for each service provider, in accordance with at least one embodiment of the present disclosure.

The methods and apparatus disclosed herein provide an operative system for personally identifiable information (PII) disclosure detection.

As previously mentioned above, currently, personal information and/or email contact information related to users is often sold or distributed to third parties after a user signs up for a web service with an internet service provider. Because a user does not know where a third party received the user's information, the user cannot make an informed decision regarding whether to share their information when signing up for a web service. The present disclosure provides a technique for tracking internet service providers that disseminate user personal information, and provides users with information regarding which internet service providers are disseminating user personal information. As such, the present disclosure solves the problem of identifying which source (e.g., internet service provider) shares or sells, either intentionally or otherwise (e.g., the internet service provider's website is hacked), email addresses or PII to a third party (e.g., another internet service provider) without the approval of the users themselves. The present disclosure also provides an assessment of risk of information disclosure for a given service provider to users. This information can be used to generate trustworthiness ratings for various service providers and other third parties.

The system and method of the present disclosure use a combination of email address aliases, PII association, and PII alteration to track and determine which web service providers are sharing PII with other organizations. In particular, the disclosed method and system use email address aliases to determine which service provider is sharing email data. The email address aliases are combined with real or partially-real PII that is attributed the receiving service provider. If a third party utilizes the alias email address, the system will know where the third party obtained its information. The present disclosure also envisions aggregating all data from all users so that users will know whether there is a high risk of data sharing before signing up with a service provider.

The present disclosure provides a system and method that create a centralized account management and data analytics framework that specifically leverages the creation of alias email addresses and pseudo-randomly generated unique PII fields to set up new accounts with online service providers of all types. The system then monitors the source and destination email addresses within email headers and email content. The system determines if service providers have sold or transferred PII or email addresses to third parties. Once a legitimate source email address has been linked to a service provider, if an email is sent from another source using that source email address, the system will automatically alert the user that their account email address is being shared with another provider. Furthermore, should unique PII be found in any email that corresponds to a source that was not originally provided that information, the offending site is tracked and the user is alerted accordingly. This would allow the user to more proactively protect themselves from information disclosure, PII disclosure, and unwanted spam email. Furthermore, this data can be aggregated across multiple users of the service to develop a quantitative level of risk associated with each service provider and also to create a network of service provider information sharing relationships. This information can be provided to new users before registering for a site, thus providing them with relevant information that may protect them from interaction with an untrustworthy party. Ultimately, as service providers lose business due to lower traffic and registration, they may be motivated to change their practices, thus better protecting sensitive user data.

The present disclosure will allow a user to always know, through the registration process with a service provider, which source email addresses are legitimate. This information is compared with other aggregated sources to determine if the service provider is a whitelisted provider to that email address (e.g., if a service provider is given access by the user to the email address). A user will be able to know which source gave up their email and, as such, the user may act on that evidence to distrust that source (e.g., blacklist the source), or the user may follow up for an explanation or develop information to take legal action. If the user's account information is compromised, the user can quickly destroy the alias email address to no longer receive email. The user can quickly create an alias email and password customized for that source.

The present disclosure as a whole can aggregate the frequency by which certain sources share information and then forewarn users of risks of disclosure when opening an account with a new service. These results can be made publically available to help manage the perception of sources and stimulate change. Users can also manually whitelist and blacklist sources. This data can be non-attributable to the users specifically and shared amongst all users of the service (e.g., machine learning), to further aggregate information and to provide a registration warning for each service. The present disclosure also covers the ability to hook into existing email addresses by analyzing email traffic to determine legitimate relationships between service providers (whitelisting/blacklisting analysis). The present disclosure also allows for keeping track of any PII that the user has provided to other service providers. Software evaluates the sent data (or form data) that tends to be PII and asks the user to verify if the data is critical. The user may assign varying levels of importance to their personal data that will feed into an overall threshold mechanism. If a real name, address, etc. is not required, the system can input unique/random data (e.g., pseudo PII) into the personal information fields for tracking.

In the following description, numerous details are set forth in order to provide a more thorough description of the system. It will be apparent, however, to one skilled in the art, that the disclosed system may be practiced without these specific details. In the other instances, well known features have not been described in detail so as not to unnecessarily obscure the system.

Embodiments of the present disclosure may be described herein in terms of functional and/or logical components and various processing steps. It should be appreciated that such components may be realized by any number of hardware, software, and/or firmware components configured to perform the specified functions. For example, an embodiment of the present disclosure may employ various integrated circuit components (e.g., memory elements, digital signal processing elements, logic elements, look-up tables, or the like), which may carry out a variety of functions under the control of one or more processors, microprocessors, or other control devices. In addition, those skilled in the art will appreciate that embodiments of the present disclosure may be practiced in conjunction with other components, and that the system described herein is merely one example embodiment of the present disclosure.

For the sake of brevity, conventional techniques and components related to PII disclosure detection, and other functional aspects of the system (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

FIG. 1 is a diagram 100 showing the disclosed system for personally identifiable information (PII) disclosure detection, where an email address and/or PII is matched for each service provider 160A-E, in accordance with at least one embodiment of the present disclosure. It should be noted that in some embodiments of the present disclosure, a postal address may be utilized instead of, or in addition to, an email address.

In this figure, a computer 120 comprising a display screen 125 is shown to be related to a user 110. The computer 120 is shown to be communicating with an application server 140 via the internet 130. The application server 140, which comprises at least one processor, is shown to be running an alias data analytics service (ADAS) application(s). The application server 140 is shown to send specific user information 150A-E to each service provider (e.g., first service providers) 160A-E.

During operation of the disclosed system, the user 110 desires to register with service providers 160A-E (e.g., internet service provider vendors). During the registration process with each of the service providers 160A-E, on at least a portion of the display screen 125 of the user's computer 120, the ADAS application(s) will inquire which user information 150A-E the user 110 would like to provide to that specific internet service provider 160A-E. Types of user information 150A-E to be provided include an email address and/or PII. The email address may be a usable email address for the user or an alias email address (i.e. a new alternate email address for the user). The PII may be real PII for the user or may be pseudo PII (i.e. false PII for that user).

The PII comprises various different types of personal information. The various different types of information may include, but is not limited to, a name, billing address, shipping address, home phone number, work phone number, mobile phone number, birth date, occupation, employer, employer address, income, credit card information, and/or user identification (ID). For example, the user 110 may wish to use an alias email address (for the email address) along with the user's real name (for the PII) for the user information 150A to be provided to service provider 160A. And, for another example, the user 110 may wish to use a useable email address (for the email address) along with a false name for the user (for the PII) for the user information 150B to be provided to service provider 160B.

In one or more embodiments, the ADAS application(s) will ask the user to assign a level of importance to each type of the personal information of the PII that is being provided. In other embodiments, at least one processor of the application server 140 running the ADAS application(s) will assign a level of importance to each type of the personal information of the PII that is being provided. In some embodiments, each type of the personal information of the PII will have a predefined level of importance assigned to it.

It should be noted that if the user 110 chooses to utilize an alias email address to provide to a service provider (e.g., service provider 160A), at least one processor of the application server 140 running the ADAS application(s) will generate a unique alias email address to be sent to that specific service provider. In addition, if the user 110 chooses to utilize pseudo PII (e.g., a false name for the user) to provide to a service provider (e.g., service provider 160B), at least one processor of the application server 140 running the ADAS application(s) will generate unique pseudo PII (e.g., a unique false name for the user) to be sent to that specific service provider.

It should be noted that unique pseudo PII refers to unique pseudo PII to a given user. This unique pseudo PII may or may not be unique just to that email address. In other words, the same pseudo PII could be used across various accounts of different users so long as it is unique within a given email address. Or, the unique pseudo PII could be unique across any email account, such that if the PII element was seen without the context of a given email address, the system could still identify a specific user.

After the user chooses the specific user information 150A-E the user 110 would like to provide to each specific service provider 160A-E, at least one processor of the application server 140 running the ADAS application(s) will match each specific service provider 160A-E to its corresponding specific user information 150A-E (e.g., email address and/or PII). Then, at least one processor of the application server 140 running the ADAS application(s) will record (e.g., in at least one first record) each specific service provider 160A-E and its corresponding specific user information 150A-E. It should be noted that FIG. 10A shows an exemplary first record, which will be discussed in detail below.

Figure 2:
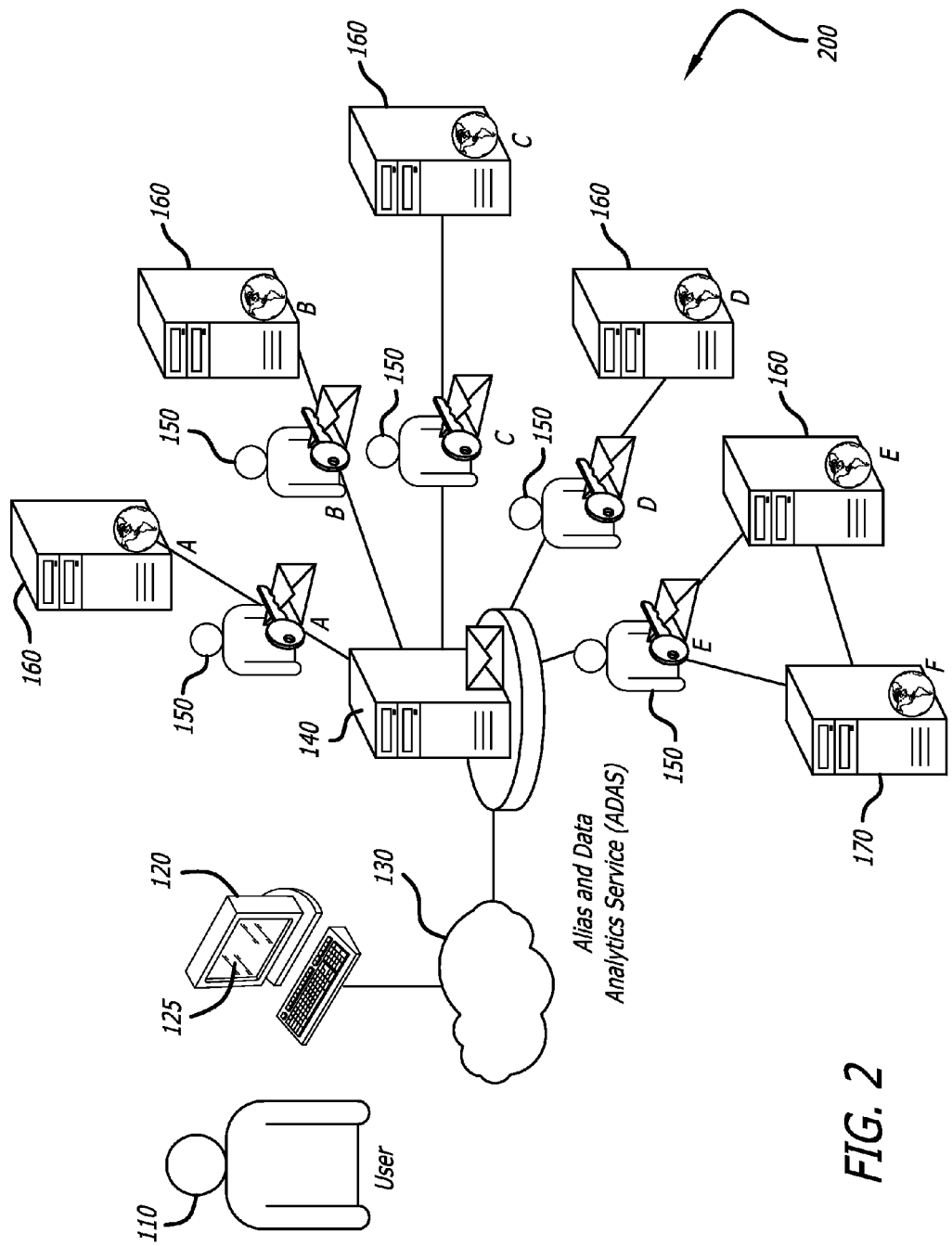
FIG. 2 is a diagram showing the disclosed system for PII disclosure detection, where the user receives an email using a matched email address and/or receives matched PII from a third party service provider, in accordance with at least one embodiment of the present disclosure.

FIG. 2 is a diagram 200 showing the disclosed system for PII disclosure detection, where the user 110 receives an email using a matched email address and/or receives matched PII (e.g., user information 150E) from a third party service provider 170F, in accordance with at least one embodiment of the present disclosure. In this figure, after at least one processor of the application server 140 running the ADAS application(s) records (e.g., in at least one first record) each specific service provider 160A-E and its corresponding specific user information 150A-E, the user 110 receives an email from a third party service provider (e.g., a second service provider) 170F using an email address of the specific user information 150E that was provided to service provider 160E and/or receives specific PII of the specific user information 150E that was provided to service provider 160E. Since the email address utilized by the third party service provider 170F to email the user 110 was only provided to service provider 160E and/or since the specific PII received by the user 110 was only provided to service provider 160E, it is clear that service provider 160E gave the third party service provider 170F the user information 150E that was provided to service provider 160E.

At least one processor of the application server 140 running the ADAS application(s) then records (e.g., in at least one first record and/or at least one second record) the third party service provider 170F that utilizes the user information 150E (e.g., a specific email address and/or specific PII) that was provided to service provider 160E. It should be noted that FIG. 10B shows an exemplary second record, which will be discussed in detail below. Then, at least one first record and/or at least one second record are stored in memory.

It should be noted that in some embodiments, the disclosed ADAS application(s) is a browser plug-in that runs locally on the user's computer 120. The ADAS browser plug-in, running locally, communicates with a centralized server (e.g., the application server 140).

Figure 3:
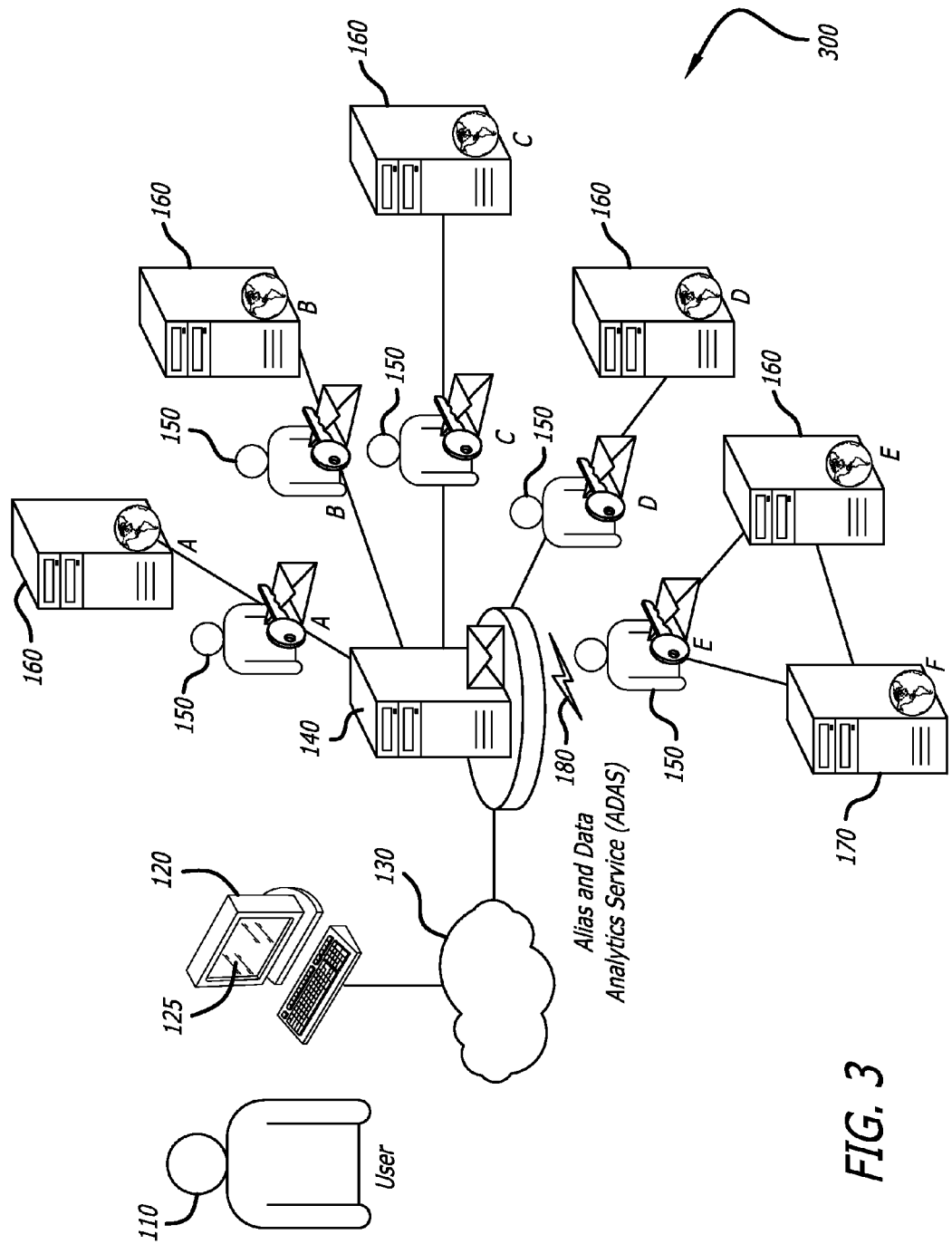
FIG. 3 is a diagram showing the disclosed system for PII disclosure detection, where the user is alerted of the disclosure of a matched email address and/or matched PII to a third party service provider, in accordance with at least one embodiment of the present disclosure.

FIG. 3 is a diagram 300 showing the disclosed system for PII disclosure detection, where the user 110 is alerted of the disclosure of a matched email address and/or matched PII to a third party service provider 170F, in accordance with at least one embodiment of the present disclosure. At least one processor of the application server 140 running the ADAS application(s) then sends an alert 180 to the user 110 (e.g., via email) notifying the user 110 that service provider 160E has provided at least a portion of its corresponding user information 150E to third party service provider 170F. At that point, the user 110 can choose to deactivate or quarantine his account with service provider 160E.

It should be noted that in some embodiments, at least one processor of the application server 140 running the ADAS application(s) sends an alert 180 to the user 110 (e.g., via email) notifying the user 110 that service provider 160E has provided at least a portion of user information corresponding to another user (not shown) to third party service provider 170F. At that point, the user 110 can choose to deactivate or quarantine his account with service provider 160E.

In one or more embodiments, at least one processor of the application server 140 running the ADAS application(s) aggregates the number of times the third party service provider 170F utilizes the email address of the specific user information 150E to email the user and/or sends the specific PII of the specific user information 150E to the user 110. Then, at least one processor of the application server 140 running the ADAS application(s) generates a ranking of trustworthiness for service provider 160E. The ranking of trustworthiness is (1) based on the number of times the third party service provider 170F utilizes the email address of the specific user information 150E to email the user and/or sends the specific PII of the specific user information 150E to the user 110; (2) based on the level of importance of the types of PII that the third party service provider 170F sends to the user 110; (3) based on the frequency that the third party service provider 170F utilizes the email address of the specific user information 150E to email the user and/or sends the specific PII of the specific user information 150E to the user 110; (4) based on the number of different third party service providers that utilize the email address of the specific user information 150E to email the user and/or send the specific PII of the specific user information 150E to the user 110; (5) based on how recently the third party service provider 170F utilized the email address of the specific user information 150E to email the user and/or sent the specific PII of the specific user information 150E to the user 110; and/or (6) based on an evolutionary trend (i.e. a trend of sharing with more third party service providers or a trend of sharing with less third party service providers) of the service provider 160E sharing, with other third party service providers, the email address of the specific user information 150E and/or the specific PII of the specific user information 150E to the user 110.

Then, the display screen 125 of the computer 120 displays the ranking of trustworthiness for the service provider 160E to the user 110. It should be noted that in one or more embodiments, the ranking of trustworthiness for a service provider 160A-E is displayed to the user 110 on the display screen 125 when the user 110 is registering for the service provider 160A-E. This allows for the user 110 to be informed of the level of trustworthiness of a service provider 160A-E when the user 110 is deciding which user information 150A-E to provide to that specific service provider 160A-E during the registration process.

Also, in one or more embodiments, the display screen 125 of the computer 120 displays a map showing the relationship for sharing user information 150E between the service provider 160E and the third party service provider 170F. It should be noted that FIG. 4 shows an exemplary map 400 showing the relationship for sharing user information between a service provider and third party service providers, which will be discussed in detail below.

Figure 4:
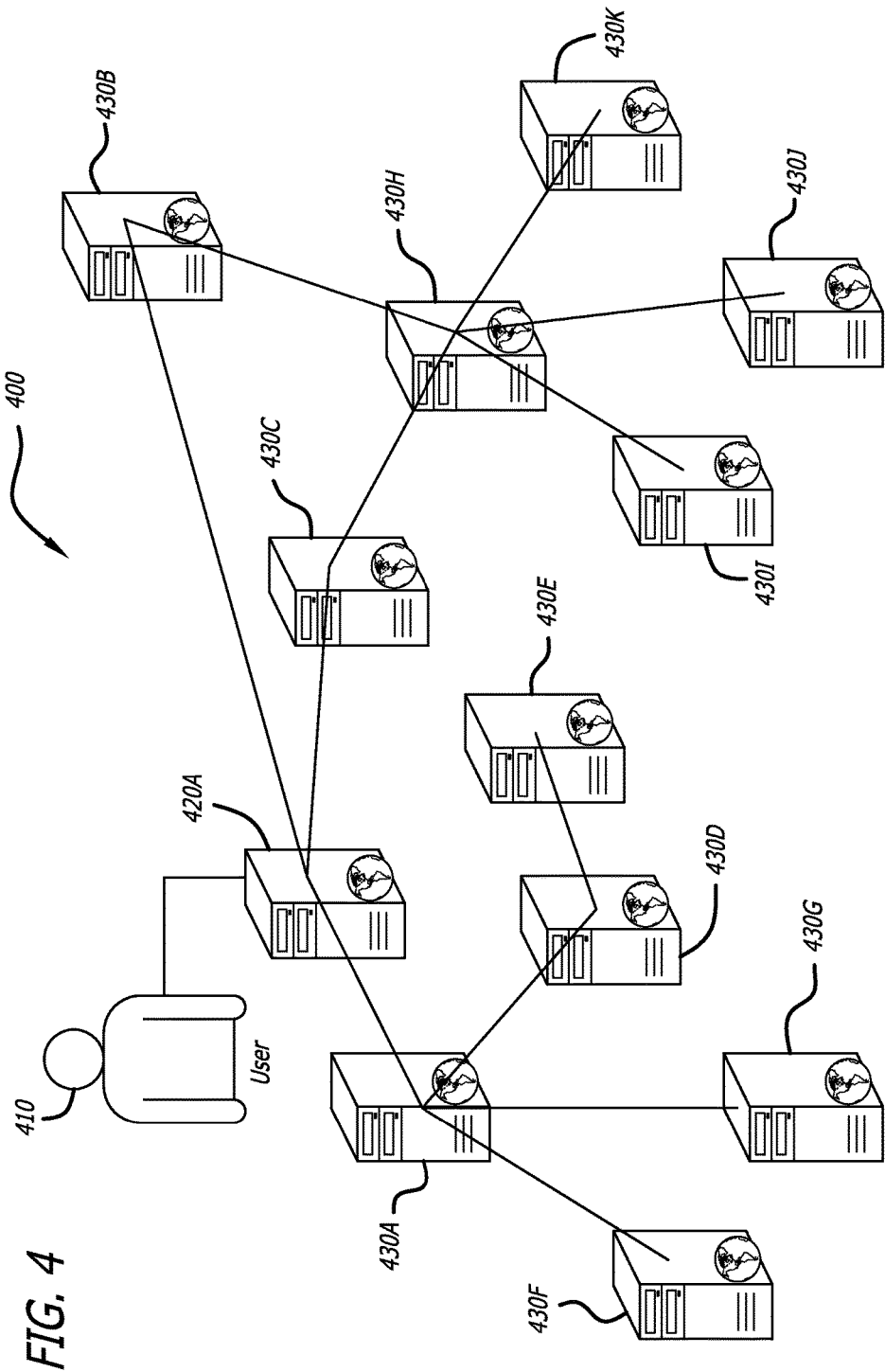
FIG. 4 is a diagram illustrating a map showing the relationship for sharing user information between a service provider and third party service providers, in accordance with at least one embodiment of the present disclosure.

FIG. 4 is a diagram illustrating a map 400 showing the relationship for sharing user information between a service provider 420A and third party service providers 430A-K, in accordance with at least one embodiment of the present disclosure. In this figure, a user 410 is shown to provide specific user information (e.g., an email address and/or PII) to service provider 420A. In turn, service provider 420A is shown to have provided the user information to third party service providers 430A-C. Third party service provider 430A is shown to have provided the user information to third party service providers 430D, F, G. And, third party service provider 430D is shown to have provided the user information to third party service provider 430E.

Also shown, third party service providers 430B, C are shown to have provided the user information to third party service provider 430H. Third party service provider 430H is shown to have provided the user information to third party service providers 430I-K. It should be noted that, over time, the disclosed system can create (and update) relationship maps of the disclosure and sharing of the user information.

It should be noted that in some embodiments, the map 400 may be filterable to show the types of information (e.g., email address, name, billing address, shipping address, home phone number, work phone number, mobile phone number, birth date, occupation, employer, employer address, income, credit card information, and/or user identification (ID)) shared between the different service providers (e.g., third party service providers 430A-K). In other embodiments, the map 400 may indicate (e.g., by being color coded and/or by including symbols) the types of information shared between the different service providers.

Figure 5B:
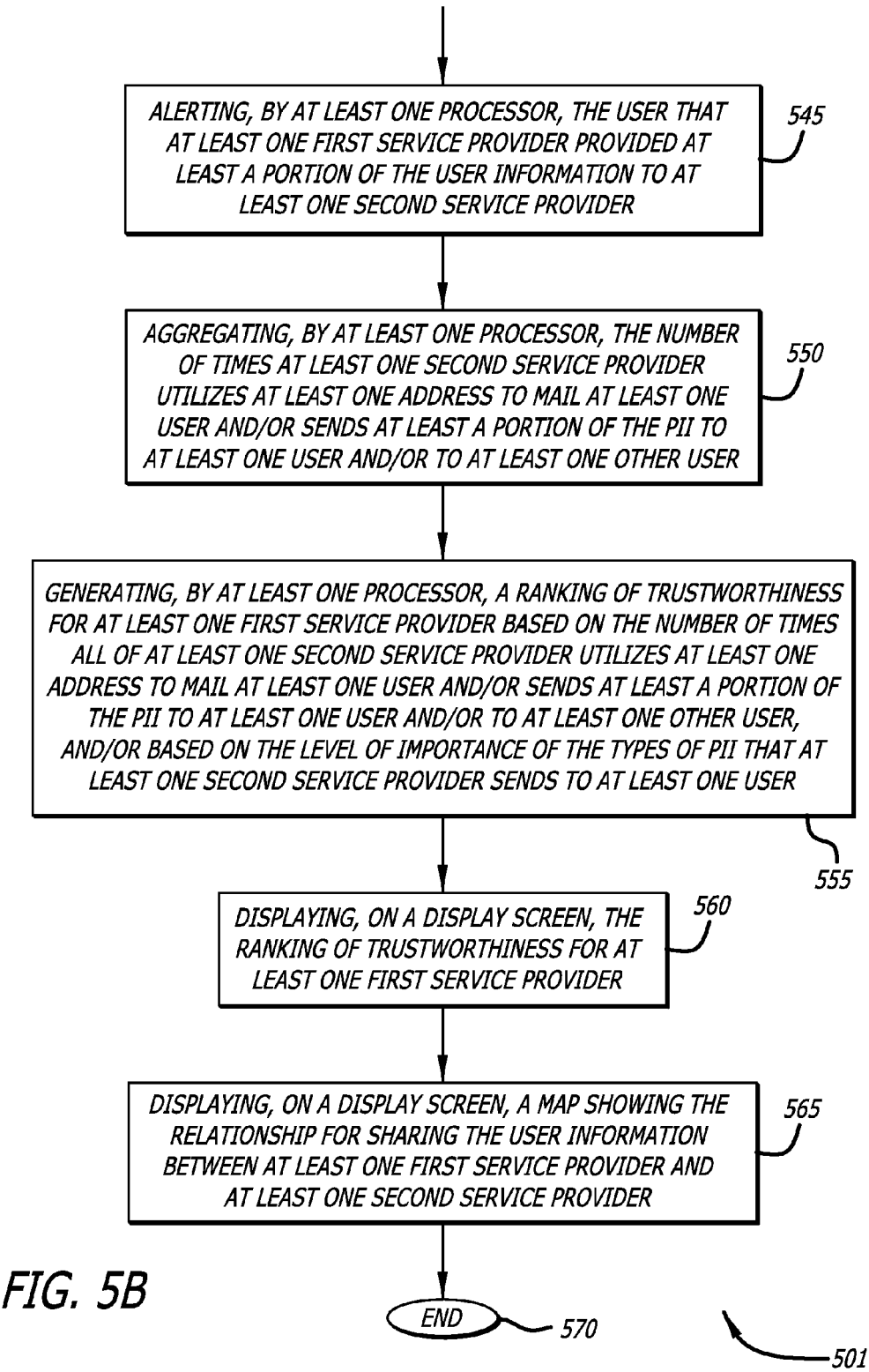

FIGS. 5A and 5B are flow charts depicting the disclosed detailed method 500, 501 for PII disclosure detection, in accordance with at least one embodiment of the present disclosure. At the start 505 of the method 500, 501, optionally, at least one processor generates an alias address related to at least one user to be used for at least one first service provider 510. At least one processor, optionally, generates pseudo PII related to at least one user to be used for at least one first service provider 515. A level of importance is assigned to each of the types of the personal information of the PII 520. Then, at least one processor matches at least one first service provider to user information (i.e. at least one address (e.g., email address and/or postal address) related to at least one user and/or PII related to at least one user) 525.

At least one processor then records (in at least one first record) at least one first service provider matched to the user information (i.e. at least one address and/or the PII) 530. Also, at least one processor records (in at least one first record and/or in at least one second record) at least one second service provider that utilizes at least one address to mail at least one user and/or sends the PII to at least one user and/or to at least one other user 535. Then, at least one first record and/or at least one second record are stored in memory 540.

At least one processor alerts the user that at least one first service provider provided at least a portion of the user information to at least one second service provider 545. At least one processor then aggregates the number of times at least one second service provider utilizes at least one address to mail at least one user and/or sends at least a portion of the PII to at least one user and/or to at least one other user 550.

Then, at least one processor generates a ranking of trustworthiness for at least one first service provider based on the number of times all of at least one second service provider utilizes at least one address to mail at least one user and/or sends at least a portion of the PII to at least one user and/or to at least one other user, and/or based on the level of importance of the types of PII that at least one second service provider sends to at least one user 555. A display screen then displays the ranking of trustworthiness for at least one first service provider 560. Also, at display screen displays a map showing the relationship for sharing user information between at least one first service provider and at least one second service provider 565. Then, the method 500, 501 ends 570.

FIGS. 6-9 show flow charts depicting various exemplary method 600, 700, 800, 900 variations that may be employed for the disclosed method of FIG. 5, in accordance with at least one embodiment of the present disclosure.

Figure 6:
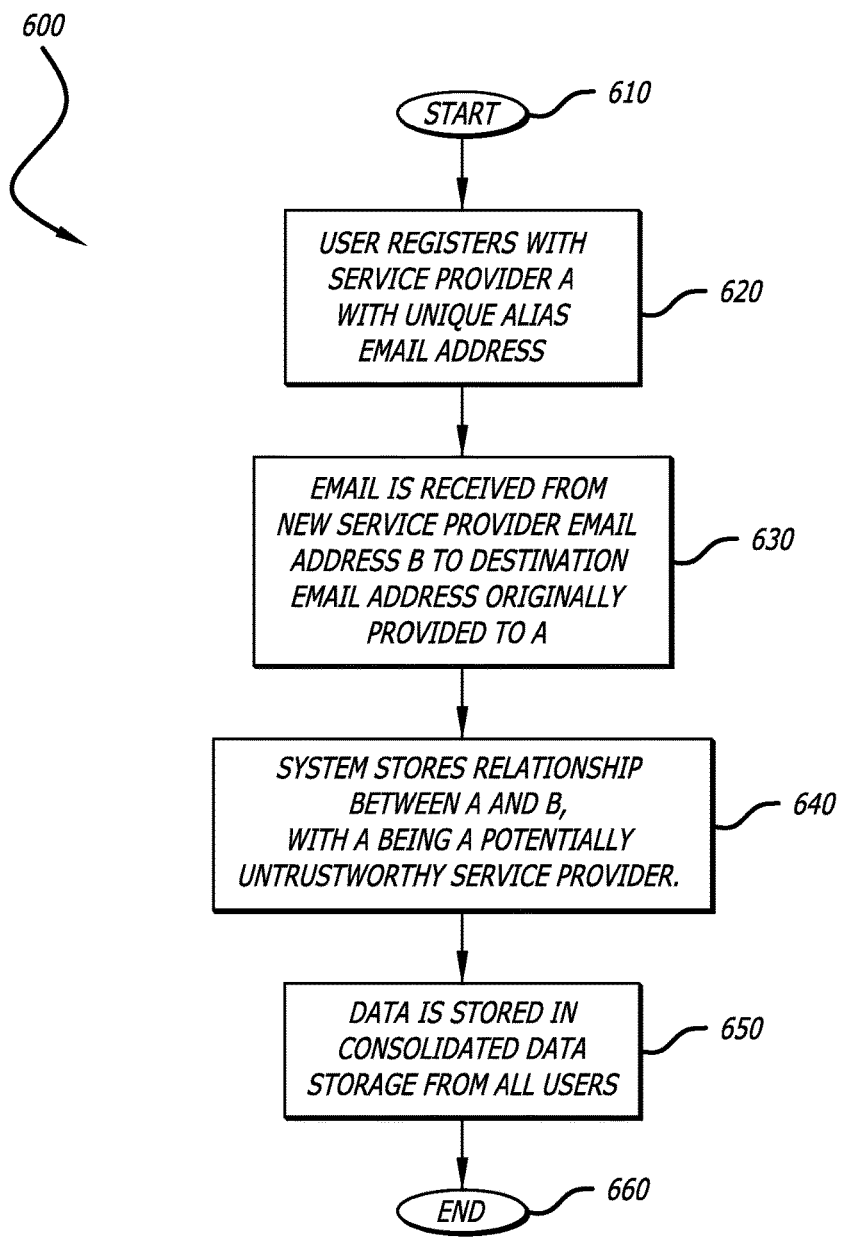
FIGS. 6-9 show flow charts depicting various exemplary method variations that may be employed for the disclosed method of FIG. 5, in accordance with at least one embodiment of the present disclosure.

FIG. 6 is a flow chart depicting the disclosed method 600 for PII disclosure detection, where a unique alias email address is matched to a service provider (e.g., service provider A), in accordance with at least one embodiment of the present disclosure. At the start 610 of the method 600, a user registers with service provider A with a unique alias email address 620. Email is received, by the user, from new service provider email address B to the destination email address originally provided to service provider A 630. The system stores the relationship between service provider A and service provider B, with service provider A being a potentially untrustworthy service provider 640. Data is stored in consolidated data storage from all users 650. Then, the method 600 ends 660.

Figure 7:
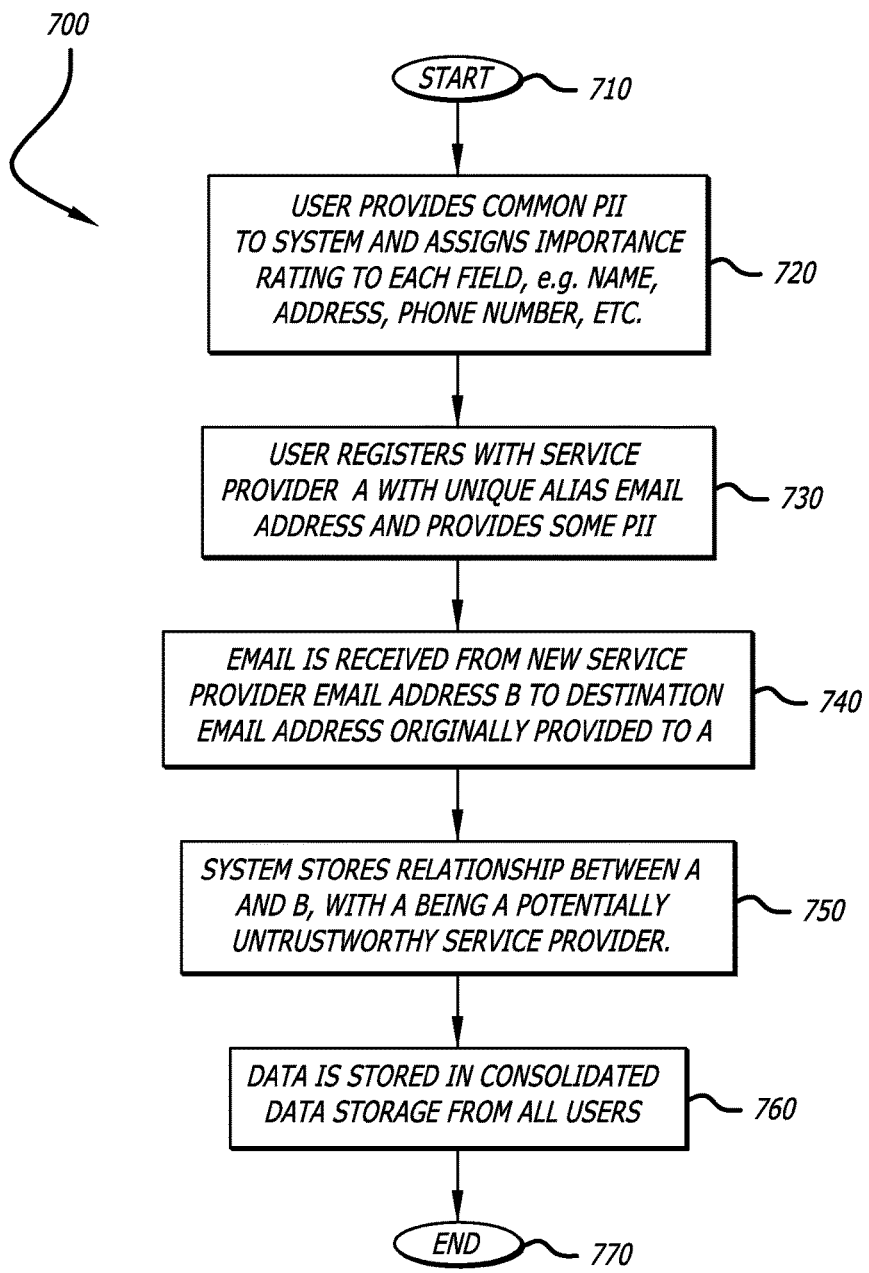

FIG. 7 is a flow chart depicting the disclosed method 700 for PII disclosure detection, where a unique alias email address and real PII is matched to a service provider (e.g., service provider A), in accordance with at least one embodiment of the present disclosure. At the start 710 of the method 700, a user provides common PII to the system and assigns an importance rating to each PII field (e.g., name, address, phone number, etc.) 720. The user registers with service provider A with a unique alias email address and provides some PII 730. Email is received, by the user, from new service provider email address B to the destination email address originally provided to service provider A 740. The system stores the relationship between service provider A and service provider B, with service provider A being a potentially untrustworthy service provider 750. Data is stored in consolidated data storage from all users 760. Then, the method 700 ends 770.

Figure 8:
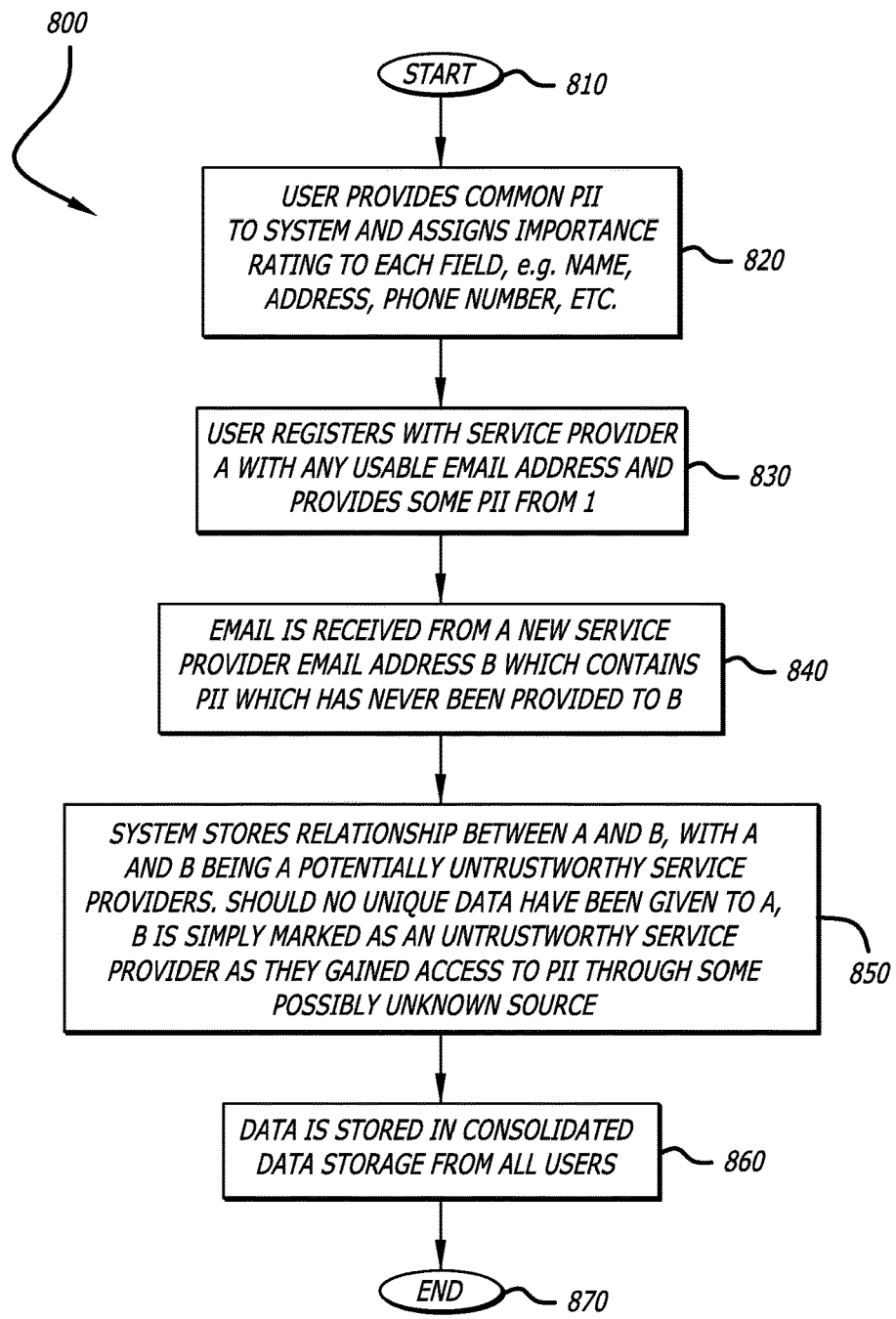

FIG. 8 is a flow chart depicting the disclosed method 800 for PII disclosure detection, where a usable email address and real PII is matched to a service provider (e.g., service provider A), in accordance with at least one embodiment of the present disclosure. At the start 810 of the method 800, a user provides common PII to the system and assigns an importance rating to each PII field (e.g., name, address, phone number, etc.) 820. The user registers with service provider A with a usable email address and provides some PII 730. Email is received, by the user, from new service provider email address B that contains some PII that has never been provided to service provider B 840. The system stores the relationship between service provider A and service provider B, with service provider A and service provider B being potentially untrustworthy service providers. Should no unique data have been given to service provider A, service provider B is simply marked as an untrustworthy service provider as they gained access to PII through some possibly unknown source 850. Data is stored in consolidated data storage from all users 860. Then, the method 800 ends 870.

Figure 9:
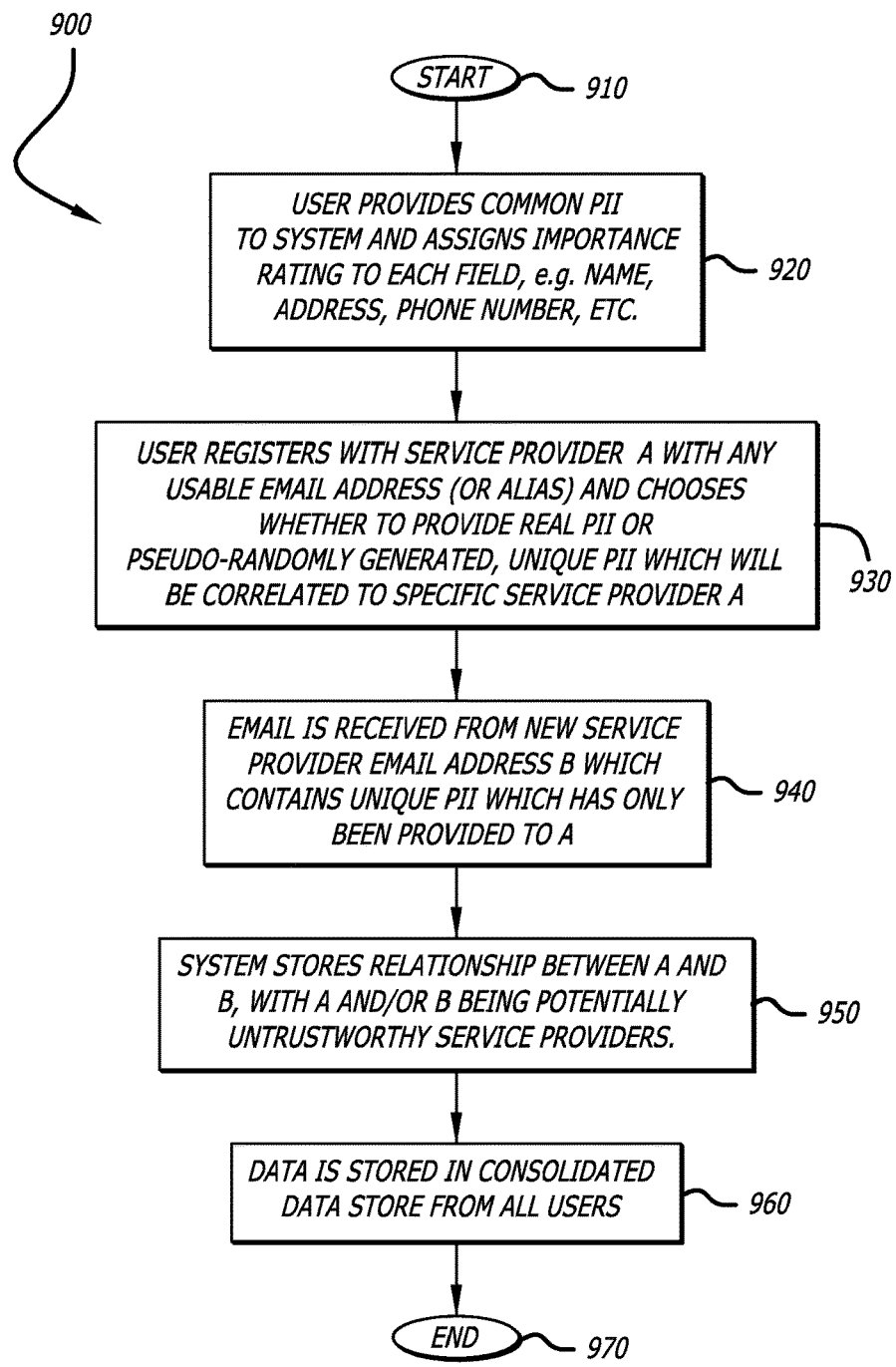

FIG. 9 is a flow chart depicting the disclosed method 900 for PII disclosure detection, where a usable email address (or alias email address) and pseudo PII is matched to a service provider (e.g., service provider A), in accordance with at least one embodiment of the present disclosure. At the start 910 of the method 900, a user provides common PII to the system and assigns an importance rating to each PII field (e.g., name, address, phone number, etc.) 920. The user registers with service provider A with a usable email address (or an alias email address) and chooses whether to provide real PII or pseudo-randomly generated, unique PII, which will be correlated to specific service provider A 930. Email is received, by the user, from new service provider email address B that contains unique PII, which has only been provided to service provider A 940. The system stores the relationship between service provider A and service provider B, with service provider A and/or service provider B being potentially untrustworthy service providers 950. Data is stored in consolidated data storage from all users 960. Then, the method 900 ends 970.

FIG. 10A is a diagram showing an exemplary first record 1000, which shows the email addresses and PII matched to service providers, that may be employed by the disclosed system for PII disclosure detection, in accordance with at least one embodiment of the present disclosure. This figure shows a table comprising seven columns and multiple rows. The first two columns represent the user's real name and the user's real email address, respectively. The third column represents the service provider name. The fourth through seventh columns represent the specific user information (i.e. the specific email address (which may be a usable email address or an alias email address) and specific PII (which may be real PII or pseudo PII (e.g., randomly generated phone numbers)) that is provided to each specific service provider. For example, the first row shows that the user's real name is "John Doe" and the user's real email address is john.doe@gmail.com. The first row also shows that for the user's name, "John Smith" (pseudo PII) is given to service provider "Store A". The first row also shows that for the user's email address, "john.doeaudDieoj@gmail.com" (an alias email address) is given to service provider "Store A".

FIG. 10B is a diagram showing an exemplary second record 1010, which shows the email addresses and/or PII received by third party service providers, that may be employed by the disclosed system for PII disclosure detection, in accordance with at least one embodiment of the present disclosure. This figure shows a table comprising nine columns and multiple rows. The first two columns represent the user's real name and the user's real email address, respectively. The third column represents the service provider name. The fourth column represents a third party service provider name. The fifth through eighth columns indicate which specific user information (e.g., the specific email address (which may be a usable email address or an alias email address) and specific PII (which may be real PII or pseudo PII)) the service provider has provided to the third party service provider. The ninth column indicates information received by the third party service provider that was not provided to the service provider. For example, the first row shows that the user's real name is "John Doe" and the user's real email address is john.doe@gmail.com. The first row also shows that the service provider "Store A" has given to third party service provider "Store F": the user name provided to the service provider, the email address provided to the service provider, the birthday provided to the first service provider, and the cell phone number provided to the service provider. Also, for example, the fifth row shows that the user's real name is "David Johnson" and the user's real email address is davidj@cox.net. The fifth row also shows that the service provider "Store E" has given to third party service provider "Store G": the user name provided to the service provider, the email address provided to the service provider, and the cell phone number provided to the service provider. And, the fifth row also shows that the user's home address, which was not initially provided to the service provider, was received by the third party service provider.

Figure 11:
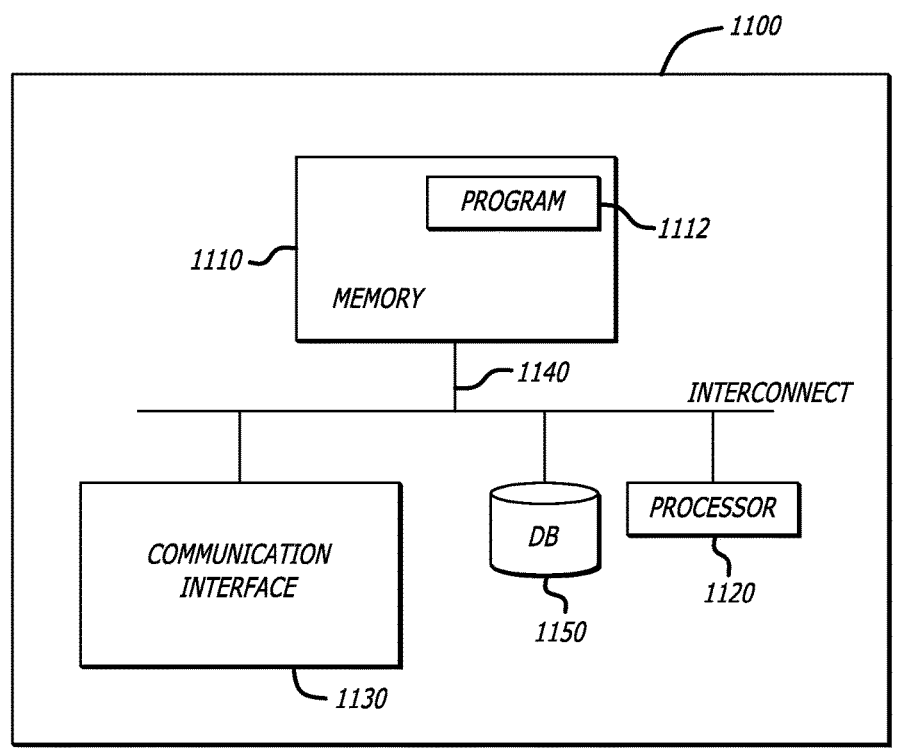
FIG. 11 is a block diagram of components of a computing apparatus or system in which various embodiments may be implemented or that may be utilized to execute embodiments.

FIG. 11 is a block diagram of components of a computing apparatus or system in which various embodiments may be implemented or that may be utilized to execute embodiments. FIG. 11 generally illustrates components of a computing device 1100 (e.g., application server 140 of FIG. 1) that may be utilized to execute embodiments and that includes a memory 1110, a program (e.g., ADAS application instructions) 1112, a processor or controller 1120 to execute the program 1112, a database 1150 for storing data (e.g., for storing at least one first record 1000 and/or at least one second record 1010), a network interface 1130, e.g., for communications with a network or interconnect 1140 between such components. The memory 1110 may be or include one or more of cache, RAM, ROM, SRAM, DRAM, RDRAM, EEPROM and other types of volatile or non-volatile memory capable of storing data. The processor unit 1120 may be or include multiple processors, a single threaded processor, a multi-threaded processor, a multi-core processor, or other type of processor capable of processing data. Depending on the particular system component (e.g., whether the component is a computer or a hand held mobile communications device), the interconnect 1140 may include a system bus, LDT, PCI, ISA, or other types of buses, and the communications or network interface may, for example, be an Ethernet interface, a Frame Relay interface, or other interface. The network interface 1130 may be configured to enable a system component to communicate with other system components across a network that may be a wireless or various other networks. It should be noted that one or more components of computing device 1100 may be located remotely and accessed via a network. Accordingly, the system configuration provided in FIG. 11 is provided to generally illustrate how embodiments may be configured and implemented.

Method embodiments may also be embodied in, or readable from, a computer-readable medium or carrier, e.g., one or more of the fixed and/or removable data storage data devices and/or data communications devices connected to a computer. Carriers may be, for example, magnetic storage medium, optical storage medium and magneto-optical storage medium. Examples of carriers include, but are not limited to, a floppy diskette, a memory stick or a flash drive, CD-R, CD-RW, CD-ROM, DVD-R, DVD-RW, or other carrier now known or later developed capable of storing data. The processor 1120 executes program instructions 1112 within memory 1110 and/or embodied on the carrier to implement method embodiments. Further, embodiments may reside and/or execute on a mobile communication device such as a cellular telephone or Smartphone.

Although particular embodiments have been shown and described, it should be understood that the above discussion is not intended to limit the scope of these embodiments. While embodiments and variations of the many aspects of the invention have been disclosed and described herein, such disclosure is provided for purposes of explanation and illustration only. Thus, various changes and modifications may be made without departing from the scope of the claims.

For example, while certain embodiments are described with products in the form of computer program products embodied in a non-transitory computer readable medium such as a software product, embodiments may also involve products in the form of tangible goods or services that are consumed by individuals and corporate and government entities.

As a further example, embodiments may involve an ADAS application that is a stand alone application, which may contain one or more programs, or that is part of another system or program.

Although particular embodiments have been shown and described, it should be understood that the above discussion is not intended to limit the scope of these embodiments. While embodiments and variations of the many aspects of the present disclosure have been disclosed and described herein, such disclosure is provided for purposes of explanation and illustration only. Thus, various changes and modifications may be made without departing from the scope of the claims.

Where methods described above indicate certain events occurring in certain order, those of ordinary skill in the art having the benefit of this disclosure would recognize that the ordering may be modified and that such modifications are in accordance with the variations of the present disclosure. Additionally, parts of methods may be performed concurrently in a parallel process when possible, as well as performed sequentially. In addition, more parts or less part of the methods may be performed.

Accordingly, embodiments are intended to exemplify alternatives, modifications, and equivalents that may fall within the scope of the claims.

Although certain illustrative embodiments and methods have been disclosed herein, it can be apparent from the foregoing disclosure to those skilled in the art that variations and modifications of such embodiments and methods can be made without departing from the true spirit and scope of the art disclosed. Many other examples of the art disclosed exist, each differing from others in matters of detail only. Accordingly, it is intended that the art disclosed shall be limited only to the extent required by the appended claims and the rules and principles of applicable law.

We claim:

1. A method of tracking user information dissemination, the method comprising:
    matching, by at least one processor, at least one first service provider to at least one of at least one address related to at least one user or personal identifiable information (PII) related to the at least one user;
    aggregating, by the at least one processor, a number of times at least one second service provider at least one of utilizes the at least one address to mail the at least one user or sends at least a portion of the PII to at least one of the at least one user or at least one other user;
    generating, by the at least one processor, a ranking of trustworthiness for the at least one first service provider based on the number of times all of the at least one second service provider at least one of utilizes the at least one address to mail the at least one user or sends at least a portion of the PII to at least one of the at least one user or the at least one other user; and
    displaying, on a display screen, a map showing the at least one user sharing the user information with the at least one first service provider and showing the at least one first service provider sharing, without approval from the at least one user, the user information with the at least one second service provider,
    wherein the user information is the at least one address related to the at least one user, at least a portion of the PII related to the at least one user, or a combination thereof.

2. The method of claim 1, wherein the method further comprises recording, by the at least one processor, the at least one first service provider matched to the at least one of the at least one address or the PII.

3. The method of claim 2, wherein the method further comprises recording, by the at least one processor, the at least one second service provider that at least one of utilizes the at least one address to mail the at least one user or sends the PII to the at least one user.

4. The method of claim 3, wherein the at least one processor records, in at least one first record, the at least one first service provider matched to the at least one of the at least one address or the PII; and
    wherein the at least one processor records, in at least one second record, the at least one second service provider that at least one of utilizes the at least one address to mail the at least one user or sends at least a portion of the PII to the at least one user.

5. The method of claim 3, wherein the at least one processor records, in at least one first record, the at least one first service provider matched to the at least one of the at least one address or the PII; and
    wherein the at least one processor records, in the at least one first record, the at least one second service provider that at least one of utilizes the at least one address to mail the at least one user or sends at least a portion of the PII to the at least one user.

6. The method of claim 1, wherein the at least one address is at least one of an email address or a postal address.

7. The method of claim 1, wherein the at least one address is at least one of a usable address or an alias address.

8. The method of claim 7, wherein the method further comprises generating, by the at least one processor, the alias address related to the at least one user to be used for the at least one first service provider.

9. The method of claim 1, wherein the PII is at least one of real PII or pseudo PII.

10. The method of claim 9, wherein the method further comprises generating, by the at least one processor, the pseudo PII related to the at least one user to be used for the at least one first service provider.

11. The method of claim 1, wherein the PII comprises different types of personal information.

12. The method of claim 11, wherein the types of personal information comprise at least one of a name, billing address, shipping address, home phone number, work phone number, mobile phone number, birth date, occupation, employer, employer address, income, credit card information, or user identification (ID).

13. The method of claim 11, wherein the method further comprises assigning a level of importance, of varying levels of importance, to each of the types of the personal information of the PII.

14. The method of claim 13, wherein the ranking of trustworthiness for the at least one first service provider is further based on the level of importance of the types of personal information of the PII that the at least one second service provider sends to the at least one user.

15. The method of claim 1, wherein the method further comprises displaying, on the display screen, the ranking of trustworthiness for the at least one first service provider.

16. A system of tracking user information dissemination, the system comprising:

at least one processor to match at least one first service provider to at least one of at least one address related to at least one user or personal identifiable information (PII) related to the at least one user; to aggregate a number of times at least one second service provider at least one of utilizes the at least one address to mail the at least one user or sends at least a portion of the PII to at least one of the at least one user or at least one other user; and to generate a ranking of trustworthiness for the at least one first service provider based on the number of times all of the at least one second service provider at least one of utilizes the at least one address to mail the at least one user or sends at least a portion of the PII to at least one of the at least one user or the at least one other user; and a display screen to display a map showing the at least one user sharing the user information with the at least one first service provider and showing the at least one first service provider sharing, without approval from the at least one user, the user information with the at least one second service provider, wherein the user information is the at least one address related to the at least one user, at least a portion of the PII related to the at least one user, or a combination thereof.

17. The system of claim 16, wherein the at least one processor is further to record the at least one first service provider matched to the at least one of the at least one address or the PII.

18. The system of claim 17, wherein the at least one processor is further to record the at least one second service provider that at least one of utilizes the at least one address to mail the at least one user or sends the PII to the at least one user.

19. The system of claim 16, wherein the display screen is to further display the ranking of trustworthiness for the at least one first service provider.

20. The method of claim 1, wherein the map is filterable to show at least one type of the user information that is shared.

21. The method of claim 1, wherein the map indicates at least one type of the user information that is shared by using at least one color code, at least one symbol, or a combination thereof.

* * * * *